United States Patent [19]

Amiguet

[11] Patent Number: 5,288,856
[45] Date of Patent: Feb. 22, 1994

[54] METHOD OF ISOLATING ACID-STABLE, BIOLOGICALLY ACTIVE PROTEINS

[76] Inventor: Pierre Amiguet, Ruelle de Cojonnex 8, CH-1807 Blonay, Switzerland

[21] Appl. No.: 854,336

[22] Filed: Mar. 19, 1992

Related U.S. Application Data

[63] Continuation of Ser. No. 436,253, Nov. 13, 1989, abandoned, which is a continuation-in-part of Ser. No. 122,012, Nov. 18, 1987, abandoned.

[30] Foreign Application Priority Data

Nov. 20, 1986 [FR] France .................................. 86 16166

[51] Int. Cl.$^5$ .............................................. C07K 3/24
[52] U.S. Cl. ..................................... 530/419; 530/344; 530/322; 530/420; 530/372; 530/395; 530/412; 530/417; 530/418; 530/422
[58] Field of Search ............... 530/344, 419, 420, 322, 530/372, 395, 412, 417, 418, 422

[56] References Cited

U.S. PATENT DOCUMENTS 4,043,990  8/1977  Melachouris ........................ 530/416
4,089,848  5/1978  Bell et al. ............................ 530/372

FOREIGN PATENT DOCUMENTS 1576763  6/1969  France .
2607137  5/1988  France .
8201641  5/1982  PCT Int'l Appl. .

OTHER PUBLICATIONS

Odani, et al., J. Biochem., vol. 82, pp. 1513–1522 (1977).
Yoshikawa, et al., J. Biochem., vol. 87, pp. 619–627 (1986).
Hamelin, et al., Chem. Abs., vol. 93 entry #40799, (1980).
Brandao, et al., Chem. Abs., vol. 108, entry #220530m (1988).

*Primary Examiner*—Michael G. Wityshyn
*Assistant Examiner*—C. Sayala
*Attorney, Agent, or Firm*—Steinberg & Raskin

[57] ABSTRACT

A method of isolating cystine rich acid-stable, biologically active proteins comprising the steps of co-precipitation by acidification of said proteins together with at least one acid-sensitive protein; isolation of said proteins from the co-precipitate by its resuspension in aqueous solution and the subsequent recovery of the proteins from the supernatant.

8 Claims, No Drawings

METHOD OF ISOLATING ACID-STABLE, BIOLOGICALLY ACTIVE PROTEINS

This is a continuation of application Ser. No. 07/436,253, filed Nov. 13, 1989, which is a continuation-in-part of Ser. No. 07/122,012, filed Nov. 18, 1987, both abandoned.

BACKGROUND OF THE INVENTION

The present invention relates to a method of isolating biologically active proteins which are acid-stable. The proteins are isolated from a biological extract of animal, vegetal or microbial origin.

The invention is in particular applicable for isolating on an industrial scale certain low molecular weight proteins the possible use of which in the pharmaceutical and food industry has been recently recognized.

Hitherto, the isolation of such proteins invariably required one or more chromatographic separation steps using, for example, ion exchange, gel permeation or affinity chromatography, which not only have the disadvantage of being very slow and very expensive but the application of which on a large scale is moreover limited for technical reasons.

OBJECTS AND SUMMARY OF THE INVENTION

The main object of the present invention is to provide a method of isolating acid-stable, biologically active proteins containing less than about 10% by dry weight of non proteinic contaminating agents only.

To achieve this goal, the method of isolation according to the present invention is characterized in that it comprises:

co-precipitation from an extract of at least one protein to be isolated together with at least one acid-sensitive protein having a molecular weight greater than 15,000 daltons; said co-precipitate being obtained by acidification of said extract;

isolation of said proteins from the co-precipitate thus formed by resuspending said co-precipitate in an aqueous solution and by subsequently discarding the remaining insoluble material.

The method according to the present invention for the isolation of acid-stable proteins very advantageously replaces the chromatographic purification steps prescribed in prior publications and patents relating to the isolation of biologically active pure proteins. The isolation method according to the present invention therefore allows very substantial gains in time and cost which make its use on an industrial scale very advantageous.

DETAILED DESCRIPTION

The invention will be better understood and further aims, characterizing features, details and advantages thereof will appear more clearly as the following explanatory description proceeds.

Moreover, the term "acid-stable protein" as used in explanation of the present invention, defines any protein the structure and the biological activity of which are not altered irreversibly in an acid medium or under the action of an acid chemical agent.

The term "co-precipitation" as used in explanation of the present invention defines the operation step according to which a soluble substance is precipitated by the sole fact that it is physically entrapped within a coagulating substance made insoluble.

The term "co-precipitate" as used in explanation of the present invention is defined by a coagulate consisting of both denatured acid-sensitive protein and acid-stable biologically active proteins which are physically entrapped in the former.

The method of the present invention is particularly suitable for the isolation of proteins having a rigid structure. As a general rule, increased structural rigidity is due to the presence within the structure of the proteins, of one or several bonds between two atoms of sulphur commonly referred to as "disulphide bridge". These bridges are provided between two cysteins present in the molecule thereby forming a residue of cystin (or dicystein).

It is common knowledge that a relationship exists between the stability of a protein against denaturation in an acid medium and its cystin content. As a general rule, a protein can be expected to have an increased stability against denaturation by acidification, if its half-cystin content is greater than 2% with respect to its total number of amino-acid residues. However, while being a necessary requirement, this is not a sufficient requirement, and it is therefore necessary to determine experimentally in each case whether a particular protein with an increased cystin content, is actually acid-stable.

By way of non-limiting examples, table 1 shows a number of proteins which meet the aforesaid structural requirement.

TABLE 1

| Protein | total number of amino-acids | di-sulphide bridges | half-cystin [%] |
|---|---|---|---|
| Calcitonin | 14 | 1 | 14 |
| Human transforming growth factor (hTGF) | 50 | 3 | 12 |
| Insulin | 55 | 3 | 11 |
| Kazal Inhibitor of trypsin | 56 | 3 | 11 |
| Kunitz Inhibitor of Trypsin. (Aprotinin) | 58 | 3 | 10 |
| Inhibitor of colostral trypsin | 67 | 3 | 9 |
| Bowman-Birk Inhibitor | 71 | 7 | 20 |
| Proinsulin | 81 | 3 | 7 |
| Neurophysin | 97 | 7 | 14 |
| Ribonuclease | 124 | 4 | 6 |
| Lysozyme | 129 | 4 | 6 |

It is noteworthy that the number of acid-stable proteins is extremely small if compared with the number of known proteins.

It is all the more surprising that, although to date few are known, several of these acid-stable proteins, are currently used as drugs, among which are insulin and aprotinin, while others, in particular various growth factors, are at present actively investigated for their possible effect in the treatment of a variety of diseases.

Certain biological extracts may well contain more than one of these proteins which then are isolated simultaneously. This is thus the case with colostrum which contains the colostral inhibitor along with alpha-lactalbumin, a homologue of lysozyme.

Table 1 also shows that it is the low molecular weight proteinase inhibitors which constitute so far the greater part of the acid-stable natural proteins. Other inhibitors, most of which are genetic homologues of those given in Table 1, have been isolated from such various sources as potatoes, snails, tortoise eggs and snake venom. The exceptional acid-stability and resistance against acid- as well as heat-denaturation of this group of proteins have been known for a long time and they are particularly suitable for practicing the method of isolation according to the present invention.

The essential operating step of the method according to the invention is the co-precipitation, from a solution or a suspension, of the acid-stable proteins and of at least one acid-sensitive protein. The present invention is indeed based upon the discovery that proteins having a molecular weight not exceeding 15,000 daltons and which are acid-stable are co-precipitated by acidification in the presence of an acid-sensitive protein having a molecular weight higher than that of the proteins to be isolated and that it is thus possible to isolate these proteins as co-precipitate from a liquid phase by centrifugation or filtration. This operation step is impossible in the absence of an acid-sensitive protein since the proteins which are acid-stable would then remain in solution after acidification.

The invention is moreover based upon the discovery that after said co-precipitation step, the proteins to be isolated can be obtained electrophoretically pure, containing less than about 10% by weight of non-proteinic contaminating agents by resuspending the pelleted co-precipitate within an aqueous solution. By this operation step, the proteins are released in solution and may thus be isolated by elimination of the insoluble material still present, in particular by centrifugation or filtration.

In the method according to the present invention, the operating steps of co-precipitation and resuspension of the recovered co-precipitate, as will become understandable hereinafter, are used with a double aim:

the removal of all acid-soluble contaminants which remain in and are discarded with the supernatant, the elimination of residual contaminating denatured proteins having a molecular weight higher than about 5,000, by an irreversible denaturation.

Typically, the co-precipitation step is carried out on crude extracts or pre-purified solutions containing the acid-stable proteins. Such pre-purifying steps depend upon the origin of the proteins to be isolated. Generally, oils and fats should be first removed when using milk, oilseeds or organs as source material. This is carried out according to conventional procedures for instance such as centrifugation in the case of milk or extraction with a solvent in the case of oilseeds and of animal organs by using solvents such as acetone, hexane or certain halogenated hydrocarbons.

Another preliminary purification may be carried out, if desired, by filtration, centrifugation and other like operating steps as well as by a combination of these operating steps and consecutive recovery of the solid or liquid phase which contains the proteins to be isolated.

These steps of pre-purification may also comprise operating steps such as ultra- and diafiltration, electrodialysis, precipitation by ammonium sulfate and any other similar operating step as well as combinations thereof. However, as is understandable, any purification step based upon chromatographic separation such as gel permeation, ion exchange, hydrophobic interaction or affinity chromatography should be avoided since these techniques are slow and expensive such that they do not lend themselves to a use on an industrial scale, and in consequence would not be in support of the present invention.

The purpose of any purification step prior to the co-precipitation step is to prepare the proteins to be isolated in an optimal condition for the subsequent co-precipitation step. For that purpose, the proteins to be isolated are generally purified to a degree of purity of at least 1% and preferably above 10% based on dry matter, by any standard purification method except those using chromatography of any type such as gel permeation, ion exchange or affinity chromatography. Moreover, the pre-purified solution or suspension containing the acid-stable proteins should preferably exhibit a total content of dry matter inclusive of the acid-sensitive protein of at least 5% and not exceeding about 30%, preferably about 15% to 20%.

According to the invention, the acid-sensitive protein may be either exogenous as, for instance, a milk protein added to an extract from pig pancreas or endogenous as, for instance, a soy protein added to a soy extract.

Proteins particularly suitable for the co-precipitation step should be selected among the proteins with a molecular weight higher than 15,000, preferably having an isoelectric point of between 2 and 6 and which are insoluble at their isoelectric point in water having an ionic strength of 0.1 or less.

A protein available in large amounts and at a low price should of course be chosen.

The preferred acid-sensitive protein is casein, such as the commercially available casein know as "Hammersten casein" after having been brought into aqueous solution at a pH between about 6 and 8. As an alternative, reserve proteins from leguminous seeds are also suitable for the present purpose. One such product is also widely commercially available under the designation "soy isolate".

These preferred proteins are obtained by removing the fat from milk and soy, respectively, and by subsequently precipitating the protein from an aqueous solution at the pH of their isoelectric point between pH 4 and 5.

According to the invention, the said acid-sensitive protein is added to the solution or suspension containing the proteins to be isolated either in a dry form or as a concentrated solution. The final concentration should be from 1% to 15% by weight per volume and preferably from 5% to 10%.

The co-precipitation is carried out by rapid acidification of the solution or of the suspension containing the proteins to be isolated while adding an effective amount of a strong acid until obtaining a pH in the range of 0 and 5 and preferably between 1.5 and 3.5.

A preferred acid is an acid likely to denature the acid-sensitive protein, i.e. adapted to make this protein irreversibly insoluble. In this respect, the preferred acid is trichloroacetic acid.

The co-precipitate obtained is recovered by centrifugation or filtration and then again suspended within about 10 volumes of an aqueous solution consisting preferably of distilled water. The insoluble material is then finely dispersed by strong stirring by means of a suitable mixer and the acid-stable proteins are then released into the solution. It is then possible to separate the suspended insoluble material by centrifugation or filtration and to concentrate the soluble phase containing the proteins, for instance by evaporation, thus obtaining a concentrate, which is practically devoid of contaminating agents having a molecular weight greater than about 5,000 and which contains less than about 10% by weight of low molecular weight, dialysable material. This material can further be removed for instance by dialysis.

It should be pointed out that the use of trichloroacetic acid is particularly advantageous since this acid has the additional property of eliminating germs possibly present in the proteins to be isolated. Thus, the invention allows the yield of proteins having a very reduced germ content since, during the co-precipitation step, these germs are killed by the trichloroacetic acid and removed from the suspension at the same time as the other insoluble material.

DETAILED DESCRIPTION OF THE PREFERRED EMBODIMENTS

The following examples given by way of illustration only will allow a better appreciation of the advantages of the method according to the invention.

EXAMPLE 1

Isolation of the Bowman-Birk Inhibitor of Proteinase from Soy

Dehulled soy beans (Fiskeby V variety, Thompson and Morgan (Ipswich) Ltd.) have been finely crushed and defatted by extraction with hexane in a Shoxlett apparatus. 500 g of the powder thus obtained which contained less than 1% of fat were twice extracted with 10 volumes of a solution containing 7 parts of ethanol and 3 parts of water (volume/volume). After centrifugation, the supernatant was discarded and the residue was twice extracted with 10 volumes of a solution containing 4 parts of ethanol and 6 parts of water (volume/volume). After centrifugation, the pellet was discarded and the supernatant concentrated about 10 times under vacuum, the temperature being kept below 50° C. Then, the yellowish solution was clarified by centrifugation and filtration and was ultrafiltrated on a UM 10 membrane from Diaflo. The permeate containing about 90% of the dry matter was discarded. The retentate of about 100 ml was subsequently diafiltrated with a volume of about 100 ml and concentrated thus bringing the content of dry matter to about 10% (weight per volume).

To this solution was added lyophilized sodium caseinate to obtain a final dry matter concentration of 15%. Protein was then precipitated from this viscous solution by lowering the pH value to about 2.5-3 by means of a saturated aqueous solution of trichloroacetic acid.

The suspension was filtered under vacuum and the precipitate was suspended twice within 4 volumes of distilled water. After centrifugation, the recovered and combined supernatants were concentrated by evaporation under vacuum, dialysed and lyophilized. Alternatively, the concentrated solution was directly lyophilized, the dry powder washed with ethanol to quantitatively remove the residual trichloroacetic acid and dried again on a rotary evaporator.

Analysis

The trypsin inhibitor activity of the extracts was measured after each purification step (see Table 2) according to the following procedure:

Solution A: (tris buffer): 6.05 g of tris (hydroxymethyl)-aminomethane (Mercks) and 2.94 g of $CaCl_2.2H_2O$ dissolved in 900 ml of water. The pH was adjusted to 8.2 with HCl and the volume reduced to 1 liter with water.

Solution B: (trypsin): 10±0,01 mg of pig trypsin (NOVO Industry, Copenhague), dissolved in 10 ml of HCl, 1 mM.

Solution C (substrate): 400 mg of hydrochloride of benzoyl-L-arginin-p-nitroanilide (L-BAPA) dissolved in 1 ml of dimethyl sulfoxide and diluted to 100 ml with tris buffer (solution A).

The reaction was started by adding 500 μl of solution B to 2 ml of solution C and the resulting absorbance changes were recorded at 410 nm. Increasing amounts of inhibitor were added and the relative speeds after partial inhibition were measured. The points between 0 and 50% of inhibition were extrapolated linearly to zero speed and the corresponding volume of inhibitor solution was taken as containing a stoichiometric amount of inhibitor. Since the inhibitor activities of the Bowman-Birk inhibitor and of the prevailing Kunitz inhibitor may not be distinguished and the relative amount of inhibitors present in the soy was still subject to controversy, it is not meaningful to express the inhibitor activity found in the extracts in weight units.

TABLE 2

| Flow sheet of example 1 | | | |
|---|---|---|---|
| | volume [ml] | dry matter | | yield [inhibitor units]* |
| | | [g] | [% from 500 g] | |
| ethanol extracts of 500 g defatted soy meal | 8200 | 48.8 | 9.76 | 22,600 |
| concentrate | 700 | 48.8 | 9.76 | 21,900 |
| UF retentate | 75 | 6.8 | 1.36 | 19,100 |
| co-precipitate extracted | 100 | 0.6 | 0.12 | 1510 |
| lyophilizate | | 0.505 | 0.1 | 1510 |

*1 inhibitor unit is defined as the amount of inhibiting activity which inhibits 1 mg of trypsin.

The final preparation of the Bowman-Birk inhibitor stoichiometrically inhibited commercial trypsin of the highest activity, i.e. 1 mg of inhibitor inhibited 3 mg of trypsin.

The analysis of the amino-acids performed on a Chromacon analyser (Kontron) according to standard procedures has revealed the number of 14 half-cystins (20% of the total number of amino-acids) which is characteristic of the inhibitors of the Bowman-Birk type.

Analysis of nitrogen (Carlo Erba): value 15.2% (theoretically 16%).

The preparation of the Bowman-Birk inhibitor has been characterized in terms of purity and molecular size by electrophoresis on a gel of polyacrylamide in the presence of 0.1% of sodium dodecylsulfate on a gel of 12.5% (20×20 cm) with a packing gel of 3%. Prior to electrophoresis, the samples (0.1 mg) were reduced with 2-mercaptoethanol. The molecular weight standards included lipoxydase (molecular weight of 98,000), beta-amylase (molecular weight of 61,000), soy lectine (molecular weight of 30,000), Kunitz soy trypsin inhibitor (molecular weight of 21,000) and alpha-lactalbumin (molecular weight of 14,800). The gel was stained with Coomassie Blue G-250 in 7% acetic acid.

According to this criterion, the Bowman-Birk inhibitor was pure and consisted, in accordance with the literature, of various homologous subspecies.

EXAMPLE 2

Isolation of the Inhibitor of Trypsin/Chymotrypsin of Bovine Lung 2.5 kg of frozen bovine lung were cut into pieces and homogenized in a Waring blender. The resulting homogenous mixture was suspended overnight in 5 liters of a solution containing 8 parts of ethanol and 2 parts of water (volume/volume). The suspension was then diluted with 2.5 l of water and centrifugated for one hour. The sediment was extracted with 5 liters of 50% ethanol in water and the supernatant obtained after centrifugation was concentrated in a rotary evaporator, the temperature not exceeding 50° C.

Subsequently, 15 g of sodium caseinate were added to 250 ml of concentrated extract and the pH was adjusted to 3.0 by rapid addition of trichloroacetic acid.

The precipitate was recovered by filtration under vacuum, extracted twice with 100 ml of distilled water and the supernatants concentrated.

The final extract containing the inhibitor was characterized in the same way as in example 1 and according to these criteria proved to be homogeneous, displaying maximal activity.

EXAMPLE 3

Purification of Alpha-Lactalbumin of Cow Colostrum 200 ml of bovine colostrum were defatted by centrifugation and the casein was removed by centrifugation at high speed.

The whey thus obtained was concentrated five times by ultrafiltration (membrane UM 5 from Diaflo) and diafiltrated with two additional volumes (80 ml) of water.

Subsequently, 4 g of sodium caseinate were added and after stirring for one hour, the pH was brought to a value of 3.0 by rapid addition of trichloroacetic acid.

The precipitate formed was filtered by means of a vacuum pump and extracted twice with distilled water.

The extract was processed and characterized as described in example 1.

Analysis by electrophoresis showed the presence of alpha-lactalbumin only. The inhibitor of colostral trypsin was not detectable although its presence could be detected in the test of inhibition of trypsin.

What is claimed is:

1. A method of isolating biologically active, acid-stable proteins from biological extracts, said acid-stable proteins having a molecular weight not exceeding 15,000 daltons and having a half-cystin content of not less than 5%, consisting of:
   co-precipitating from said extracts said acid-stable proteins to be isolated with acid-sensitive proteins having a molecular weight greater than 15,000 daltons, said co-precipitation being obtained by acidification of said extracts with a strong, protein denaturing acid such that said acid-stable proteins remain undenatured and said acid-sensitive proteins are denatured;
   isolating said undenatured acid-stable proteins from the co-precipitate thus formed by resuspending said co-precipitate in an aqueous solution, separating all insoluble material and recovering said undenatured acid-stable proteins from the aqueous phase, the residual contaminants thereof consist of nonproteinic material only in an amount of less than 10% by weight.

2. The method of claim 1, wherein said acid-sensitive proteins are exogenous.

3. The method of claim 1, wherein said acid-sensitive proteins are endogenous.

4. The method of claim 2, wherein said acid-sensitive exogenous proteins are added to said biological extracts containing said proteins to be isolated, the amount of said acid-sensitive proteins at their final concentration thereof being about 1% to 15% by weight.

5. The method of claim 1, wherein said acidification step is carried out by addition to said extract, of an acid to obtain a pH less than 5.

6. The method of claim 5, wherein the obtained pH is in the range of 1.5 to 3.5.

7. The method according to claim 1, wherein said strong acid is trichloroacetic acid.

8. A method of isolating biologically active, acid-stable proteins from biological extracts comprising acid-stable proteins and acid-sensitive proteins, comprising
   acidifying an extract comprising acid-sensitive proteins having a molecular weight greater than 15,000 daltons and acid-stable proteins selected from the group consisting of calcitonin, human transforming growth factor, insulin, Kazal Inhibitor of trypsin, aprotinin, Inhibitor of colostral trypsin, Bowman-Birk Inhibitor, proinsulin, neurophysin, ribonuclease, lysozyme, and mixtures of any of the foregoing, with a strong acid comprising trichloroacetic acid, such that a coagulation is obtained comprising said acid-stable proteins physically entrapped in said acid-sensitive proteins, said acid-stable proteins being undenatured and said acid-sensitive proteins being denatured,
   isolating said acid-stable proteins from said coagulation by resuspending said coagulation in an aqueous phase,
   separating all insoluble material and recovering said acid-stable proteins from the aqueous phase, such that the residual contaminants thereof consist of nonproteinic material only in an amount of less than 10% by weight.

* * * * *